United States Patent
Inan et al.

(10) Patent No.: US 11,643,663 B2
(45) Date of Patent: May 9, 2023

(54) DETERMINATION OF REGULATORY DNA REGIONS OF ALCOHOL DEHYDROGENASE 3 (ADH3) PROMOTER AND DESIGN OF SYNTHETIC PROMOTERS FOR RECOMBINANT PROTEIN PRODUCTION

(71) Applicant: AKDENIZ UNIVERSITESI, Antalya (TR)

(72) Inventors: Mehmet Inan, Antalya (TR); Mert Karaoglan, Erzincan (TR); Fidan Erden Karaoglan, Erzincan (TR)

(73) Assignee: AKDENIZ UNIVERSITESI, Antalya (TR)

( * ) Notice: Subject to any disclaimer, the term of this patent is extended or adjusted under 35 U.S.C. 154(b) by 0 days.

(21) Appl. No.: 16/621,221

(22) PCT Filed: Feb. 14, 2019

(86) PCT No.: PCT/TR2019/050099
§ 371 (c)(1),
(2) Date: Dec. 10, 2019

(87) PCT Pub. No.: WO2019/203769
PCT Pub. Date: Oct. 24, 2019

(65) Prior Publication Data
US 2021/0403931 A1    Dec. 30, 2021

(30) Foreign Application Priority Data

Apr. 16, 2018  (TR) .................. 2018/05404

(51) Int. Cl.
*C12N 15/81*  (2006.01)
*C12N 9/04*   (2006.01)
*C12P 21/02*  (2006.01)
*C12N 1/15*   (2006.01)

(52) U.S. Cl.
CPC ......... *C12N 15/815* (2013.01); *C12N 9/0006* (2013.01); *C12P 21/02* (2013.01); *C12Y 101/01001* (2013.01)

(58) Field of Classification Search
None
See application file for complete search history.

(56) References Cited

U.S. PATENT DOCUMENTS

2015/0011407 A1* 1/2015 Vogl ..................... C12N 15/815
                                                         506/10
2021/0309990 A1* 10/2021 Calik .................. C12N 9/0006

FOREIGN PATENT DOCUMENTS

| WO | 1997012044 | 4/1997 |
| WO | 2002081650 | 10/2002 |
| WO | 2008063302 | 5/2008 |

OTHER PUBLICATIONS

GenBank, Accession No. CP014585, 2016, www.ncbi.nlm.nih.gov. (Year: 2016).*
Uniprot, Accession No. Q6QA21, 2017, www.uniprot.org . (Year: 2017).*
GenBank, Accession No. ACJ26382.1, 2009, www.ncbi.nlm.nih.gov. (Year: 2009).*
Karaoglan, Studies on Alcohol Dehydrogenase (ADH3) Promotor in Pichia pastoris, Doctor's Thesis, Department of Food Engineering, Akdeniz University, 2016. (Year: 2016).*
Karaoglan, Studies on Alcohol Dehydrogenase (ADH3) Promotor in Pichia pastoris, Doctor's Thesis, Department of Food Engineering, Akdeniz University, 2016, English-language machine translation. (Year: 2016).*
ISR, dated Oct. 1, 2019.
Karaoglan M., Karaoglan F.E. and Inan M. "Comparison of ADH3 promoter with commonly used promoters for recombinant protein production in Pichia pastoris" Protein Expression and Purification, 121, 112-117, May 2016 (May 2016), DOI: 10.1016/j.pep.2016.01.017.
Opinion of International Search Authority, dated Oct. 1, 2019.

\* cited by examiner

*Primary Examiner* — Robert B Mondesi
*Assistant Examiner* — Todd M Epstein
(74) *Attorney, Agent, or Firm* — Crose Law LLC; Bradley D. Crose

(57) ABSTRACT

The invention relates to the ADH3 promoter; polynucleotide sequences, vectors and expression cassettes including DNA regions responsible for the regulation of the ADH3 promoter; the host cells, including these vectors and expression cassettes, and, the recombinant proteins performed with the developed cells. In the scope of the invention, deletion analyzes in the ADH3 promoter were performed to identify regions that affect promoter strength and significant data was obtained in the formation of mutant ADH3 promoters. Deletion of the nucleotides between 539 and 638 (−361 to −262) in SEQ ID NO: 1 resulted in a 63% increase in ADH3 promoter activity. Five different synthetic promoters were created using positive regulatory regions identified and approximately 165% to 200% promoter activities were achieved with these promoters.

3 Claims, 8 Drawing Sheets

Specification includes a Sequence Listing.

SEQUENCE LISTING

<160> NUMBER OF SEQ ID NOS: 52

<210> SEQ ID NO 1
<211> LENGTH: 900
<212> TYPE: DNA
<213> ORGANISM: Pichia pastoris

<400> SEQUENCE: 1

```
atgcccggag gagacttgcc ccctaatttc gcggcgtcgt cccggatcgc agggtgagac      60
tgtagagacc ccacatagtg acaatgatta tgtaagaaga gggggggtgat tcggccggct    120 atcgaactct aacaactagg ggggtgaaca atgcccagca gtcctcccca ctctttgaca    180
aatcagtatc accgattaac accccaaatc ttattctcaa cggtccctca tccttgcacc    240
cctctttgga caaatggcag ttagcattgg tgcactgact gactgcccaa ccttaaaccc    300
```

```
aaatttctta gaaggggccc atctagttag cgaggggtga aaaattcctc catcggagat    360
gtattgaccg taagttgctg cttaaaaaaa atcagttcag atagcgagac ttttttgatt    420
tcgcaacggg agtgcctgtt ccattcgatt gcaattctca ccccttctgc ccagtcctgc    480
caattgccca tgaatctgct aatttcgttg attcccaccc cccttccaa ctccacaaat     540 tgtccaatct cgttttccat ttgggagaat ctgcatgtcg actacataaa gcgaccggtg    600
tccgaaaaga tctgtgtagt tttcaacatt ttgtgctccc cccgctgttt gaaaacgggg    660
gtgagcgctc tccggggtgc gaattcgtgc ccaattcctt tcaccctgcc tattgtagac    720
gtcaacccgc atctggtgcg aatatagcgc accccaatg atcacaccaa caattggtcc     780
acccctcccc aatctctaat attcacaatt cacctcacta taaataccc tgtcctgctc     840 ccaaattctt ttttccttct tccatcagct actagctttt atcttattta ctttacgaaa    900

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
aaaggatccc gattgcccct ctacaggcat aag                                   33

<210> SEQ ID NO 3
<211> LENGTH: 29
<212> TYPE: DNA
<213> ORGANISM: Artificial Sequence
<220> FEATURE:
<223> OTHER INFORMATION: Primer

<400> SEQUENCE: 3
aaaggatcca tgcccggagg agacttgcc                                        29

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
aaaggatccg gggggtgatt cggccg                                           26

<210> SEQ ID NO 5
<211> LENGTH: 29
<212> TYPE: DNA
<213> ORGANISM: Artificial Sequence
<220> FEATURE:
<223> OTHER INFORMATION: Primer

<400> SEQUENCE: 5
aaaggatcca ccccaaatct tattctcaa                                        29

<210> SEQ ID NO 6
<211> LENGTH: 29
<212> TYPE: DNA
<213> ORGANISM: Artificial Sequence
<220> FEATURE:
<223> OTHER INFORMATION: Primer

<400> SEQUENCE: 6
```
aaaggatcca aatttcttag aaggggccc                                              29

<210> SEQ ID NO 7
<211> LENGTH: 32
<212> TYPE: DNA
<213> ORGANISM: Artificial Sequence
<220> FEATURE:
<223> OTHER INFORMATION: Primer

<400> SEQUENCE: 7
cccggatcca tagcgagact tttttgattt cg                                          32

<210> SEQ ID NO 8
<211> LENGTH: 29
<212> TYPE: DNA
<213> ORGANISM: Artificial Sequence
<220> FEATURE:
<223> OTHER INFORMATION: Primer

<400> SEQUENCE: 8
aaaggatcca atttcgttga ttcccaccc                                              29

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
aaaggatcct ccgaaaagat ctgtgtagt                                              29

<210> SEQ ID NO 10
<211> LENGTH: 29
<212> TYPE: DNA
<213> ORGANISM: Artificial Sequence
<220> FEATURE:
<223> OTHER INFORMATION: Primer

<400> SEQUENCE: 10
aaaggatcct caccctgcct attgtagac                                              29

<210> SEQ ID NO 11
<211> LENGTH: 29
<212> TYPE: DNA
<213> ORGANISM: Artificial Sequence
<220> FEATURE:
<223> OTHER INFORMATION: Primer

<400> SEQUENCE: 11
aaaggatcca ttcacaattc acctcacta                                              29

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
tttcgaaagt aaataagata aaagctagta g                                           31

<210> SEQ ID NO 13
<211> LENGTH: 27
<212> TYPE: DNA
<213> ORGANISM: Artificial Sequence

```
<220> FEATURE:
<223> OTHER INFORMATION: Primer

<400> SEQUENCE: 13
aaaggatcca gggggtgat tcggccg                                              27

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
cggtgatact gatttgtcta tgtggggtct ctacag                                   36

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
ctgtagagac cccacataga caaatcagta tcaccg                                   36

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
accaatgcta actgccatgc attgttcacc cccta                                    36

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
taggggggtg aacaatgcat ggcagttagc attggt                                   36

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18 ggaattttc acccctcgat gagggaccgt tgagaa                                    36

<210> SEQ ID NO 19
<211> LENGTH: 36
<212> TYPE: DNA
<213> ORGANISM: Artificial Sequence
<220> FEATURE:
<223> OTHER INFORMATION: Primer

<400> SEQUENCE: 19
ttctcaacgg tccctcatcg aggggtgaaa aattcc                                   36
```

```
<210> SEQ ID NO 20
<211> LENGTH: 36
<212> TYPE: DNA
<213> ORGANISM: Artificial Sequence
<220> FEATURE:
<223> OTHER INFORMATION: Primer

<400> SEQUENCE: 20
tgcgaaatca aaaagtcag aaatttgggt ttaagg                              36

<210> SEQ ID NO 21
<211> LENGTH: 36
<212> TYPE: DNA
<213> ORGANISM: Artificial Sequence
<220> FEATURE:
<223> OTHER INFORMATION: Primer

<400> SEQUENCE: 21
ccttaaaccc aaatttctga cttttttgat ttcgca                             36

<210> SEQ ID NO 22
<211> LENGTH: 36
<212> TYPE: DNA
<213> ORGANISM: Artificial Sequence
<220> FEATURE:
<223> OTHER INFORMATION: Primer

<400> SEQUENCE: 22
ttagcagatt catgggcatt aagcagcaac ttacgg                             36

<210> SEQ ID NO 23
<211> LENGTH: 36
<212> TYPE: DNA
<213> ORGANISM: Artificial Sequence
<220> FEATURE:
<223> OTHER INFORMATION: Primer

<400> SEQUENCE: 23
ccgtaagttg ctgcttaatg cccatgaatc tgctaa                             36

<210> SEQ ID NO 24
<211> LENGTH: 36
<212> TYPE: DNA
<213> ORGANISM: Artificial Sequence
<220> FEATURE:
<223> OTHER INFORMATION: Primer

<400> SEQUENCE: 24
gacatgcaga ttctcccagg tgagaattgc aatcga                             36

<210> SEQ ID NO 25
<211> LENGTH: 36
<212> TYPE: DNA
<213> ORGANISM: Artificial Sequence
<220> FEATURE:
<223> OTHER INFORMATION: Primer

<400> SEQUENCE: 25
tcgattgcaa ttctcacctg ggagaatctg catgtc                             36

<210> SEQ ID NO 26
<211> LENGTH: 36
<212> TYPE: DNA
<213> ORGANISM: Artificial Sequence
<220> FEATURE:
<223> OTHER INFORMATION: Primer
```

<400> SEQUENCE: 26
gttttcaaac agcggggtt tgtggagttg gaaagg                                        36

<210> SEQ ID NO 27
<211> LENGTH: 36
<212> TYPE: DNA
<213> ORGANISM: Artificial Sequence
<220> FEATURE:
<223> OTHER INFORMATION: Primer

<400> SEQUENCE: 27
cctttccaac tccacaaacc cccgctgttt gaaaac                                       36

<210> SEQ ID NO 28
<211> LENGTH: 36
<212> TYPE: DNA
<213> ORGANISM: Artificial Sequence
<220> FEATURE:
<223> OTHER INFORMATION: Primer

<400> SEQUENCE: 28
gatgcgggtt gacgtctaca cagatctttt cggaca                                       36

<210> SEQ ID NO 29
<211> LENGTH: 36
<212> TYPE: DNA
<213> ORGANISM: Artificial Sequence
<220> FEATURE:
<223> OTHER INFORMATION: Primer

<400> SEQUENCE: 29
tgtccgaaaa gatctgtgta gacgtcaacc cgcatc                                       36

<210> SEQ ID NO 30
<211> LENGTH: 36
<212> TYPE: DNA
<213> ORGANISM: Artificial Sequence
<220> FEATURE:
<223> OTHER INFORMATION: Primer

<400> SEQUENCE: 30
aattgtgaat attagagatg ggcacgaatt cgcacc                                       36

<210> SEQ ID NO 31
<211> LENGTH: 36
<212> TYPE: DNA
<213> ORGANISM: Artificial Sequence
<220> FEATURE:
<223> OTHER INFORMATION: Primer

<400> SEQUENCE: 31
ggtgcgaatt cgtgcccatc tctaatattc acaatt                                       36

<210> SEQ ID NO 32
<211> LENGTH: 36
<212> TYPE: DNA
<213> ORGANISM: Artificial Sequence
<220> FEATURE:
<223> OTHER INFORMATION: Primer

<400> SEQUENCE: 32 cagggggtatt tatagtgatt ggtgtgatca ttgggg                                      36

<210> SEQ ID NO 33

```
<211> LENGTH: 36
<212> TYPE: DNA
<213> ORGANISM: Artificial Sequence
<220> FEATURE:
<223> OTHER INFORMATION: Primer

<400> SEQUENCE: 33
ccccaatgat cacaccaatc actataaata cccctg                                 36

<210> SEQ ID NO 34
<211> LENGTH: 36
<212> TYPE: DNA
<213> ORGANISM: Artificial Sequence
<220> FEATURE:
<223> OTHER INFORMATION: Primer

<400> SEQUENCE: 34
gtgggaatca acgaaattgt taatcggtga tactga                                 36

<210> SEQ ID NO 35
<211> LENGTH: 36
<212> TYPE: DNA
<213> ORGANISM: Artificial Sequence
<220> FEATURE:
<223> OTHER INFORMATION: Primer

<400> SEQUENCE: 35
tcagtatcac cgattaacaa tttcgttgat tcccac                                 36

<210> SEQ ID NO 36
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 36
atgcccggag gagacttgcc ccctaatttc gcggcgtcgt cccggatcgc agggtgagac       60
tgtagagacc ccacatagtg acaatgatta tgtaagaag                              99

<210> SEQ ID NO 37
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 37
gtgacaatga ttatgtaaga agaggggggt gattcggccg gctatcgaac tctaacaact       60 agggggggtga acaatgccca gcagtcctcc ccactcttt                             99

<210> SEQ ID NO 38
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 38
ccagcagtcc tccccactct ttgacaaatc agtatcaccg attaacaccc caaatcttat       60
tctcaacggt ccctcatcct tgcacccctc tttggacaa                              99
```

<210> SEQ ID NO 39
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 39
ccttgcaccc ctctttggac aaatggcagt tagcattggt gcactgactg actgcccaac    60
cttaaaccca aatttcttag aaggggccca tctagttag                           99

<210> SEQ ID NO 40
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 40
tagaaggggc ccatctagtt agcgaggggt gaaaaattcc tccatcggag atgtattgac    60
cgtaagttgc tgcttaaaaa aaatcagttc agatagcga                           99

<210> SEQ ID NO 41
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 41
aaaaaatcag ttcagatagc gagactttt tgatttcgca acgggagtgc ctgttccatt     60
cgattgcaat tctcacccct tctgcccagt cctgccaat                           99

<210> SEQ ID NO 42
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 42
ccttctgccc agtcctgcca attgcccatg aatctgctaa tttcgttgat tcccaccccc    60
ctttccaact ccacaaattg tccaatctcg ttttccatt                           99

<210> SEQ ID NO 43
<211> LENGTH: 99
<212> TYPE: DNA
<213> ORGANISM: Artificial Sequence
<220> FEATURE:
<223> OTHER INFORMATION: Nucleic acid fragment deleted from the ADH3
      promoter

<400> SEQUENCE: 43
ttgtccaatc tcgttttcca tttgggagaa tctgcatgtc gactacataa agcgaccggt    60
gtccgaaaag atctgtgtag ttttcaacat tttgtgctc                           99

<210> SEQ ID NO 44
<211> LENGTH: 99
<212> TYPE: DNA

<213> ORGANISM: Artificial Sequence
<220> FEATURE:
<223> OTHER INFORMATION: Nucleic acid fragment deleted from the ADH3 promoter

<400> SEQUENCE: 44

```
tagttttcaa cattttgtgc tcccccgct gtttgaaaac gggggtgagc gctctccggg    60
gtgcgaattc gtgcccaatt cctttcaccc tgcctattg                          99
```

<210> SEQ ID NO 45
<211> LENGTH: 99
<212> TYPE: DNA
<213> ORGANISM: Artificial Sequence
<220> FEATURE:
<223> OTHER INFORMATION: Nucleic acid fragment deleted from the ADH3 promoter

<400> SEQUENCE: 45

```
attcctttca ccctgcctat tgtagacgtc aacccgcatc tggtgcgaat atagcgcacc    60
cccaatgatc acaccaacaa ttggtccacc cctccccaa                           99
```

<210> SEQ ID NO 46
<211> LENGTH: 44
<212> TYPE: DNA
<213> ORGANISM: Artificial Sequence
<220> FEATURE:
<223> OTHER INFORMATION: Nucleic acid fragment deleted from the ADH3 promoter

<400> SEQUENCE: 46

```
caattggtcc acccctcccc aatctctaat attcacaatt cacc                    44
```

<210> SEQ ID NO 47
<211> LENGTH: 300
<212> TYPE: DNA
<213> ORGANISM: Artificial Sequence
<220> FEATURE:
<223> OTHER INFORMATION: Nucleic acid fragment deleted from the ADH3 promoter

<400> SEQUENCE: 47

```
accccaaatc ttattctcaa cggtccctca tccttgcacc cctctttgga caaatggcag    60
ttagcattgg tgcactgact gactgcccaa ccttaaaccc aaatttctta gaagggggccc   120
atctagttag cgaggggtga aaaattcctc catcggagat gtattgaccg taagttgctg   180
cttaaaaaaa atcagttcag atagcgagac ttttttgatt tcgcaacggg agtgcctgtt   240
ccattcgatt gcaattctca cccttctgc ccagtcctgc caattgccca tgaatctgct    300
```

<210> SEQ ID NO 48
<211> LENGTH: 389
<212> TYPE: DNA
<213> ORGANISM: Artificial Sequence
<220> FEATURE:
<223> OTHER INFORMATION: Synthetic promoter

<400> SEQUENCE: 48

```
atgcccggag gagacttgcc ccctaatttc gcggcgtcgt cccggatcgc agggtgagac    60
tgtagagacc ccacatagtg acaatgatta tgtaagaagt ctagatagtt ttcaacattt   120
tgtgctcccc ccgctgtttg aaaacggggg tgagcgctct ccggggtgcg aattcgtgcc   180
caattccttt caccctgcct attgtagacg tcaacccgca tctggtgcga atatagcgca   240
ccccaatga tcacaccaac aattggtcca cccctcccca atctctaata ttcacaattc    300
```
acctcactat aaatacccct gtcctgctcc caaattctttt tttccttctt ccatcagcta    360 ctagcttttta tcttatttac tttacgaaa                                     389

<210> SEQ ID NO 49
<211> LENGTH: 466
<212> TYPE: DNA
<213> ORGANISM: Artificial Sequence
<220> FEATURE:
<223> OTHER INFORMATION: Synthetic promoter

<400> SEQUENCE: 49
tagttttcaa cattttgtgc tccccccgct gtttgaaaac gggggtgagc gctctccggg    60
gtgcgaattc gtgcccaatt cctttcaccc tgcctattgt agacgtcaac ccgcatctgg    120
tgcgaatata gcgcaccccc aatgatcaca ccaacaattg gtccacccct ccccaaaagc    180
tttagttttc aacattttgt gctcccccg ctgtttgaaa acggggggtga gcgctctccg    240 gggtgcgaat tcgtgcccaa ttcctttcac cctgcctatt gtagacgtca acccgcatct    300
ggtgcgaata tagcgcaccc ccaatgatca caccaacaat tggtccaccc ctccccaatc    360
tctaatattc acaattcacc tcactataaa taccccctgtc ctgctcccaa attctttttt    420
ccttcttcca tcagctacta gcttttatct tatttacttt acgaaa                   466

<210> SEQ ID NO 50
<211> LENGTH: 571
<212> TYPE: DNA
<213> ORGANISM: Artificial Sequence
<220> FEATURE:
<223> OTHER INFORMATION: Synthetic promoter

<400> SEQUENCE: 50
atgcccggag gagacttgcc ccctaatttc gcggcgtcgt cccggatcgc agggtgagac    60
tgtagagacc ccacatagtg acaatgatta tgtaagaagt ctagatagtt ttcaacattt    120
tgtgctcccc ccgctgtttg aaaacggggg tgagcgctct ccggggtgcg aattcgtgcc    180
caattccttt caccctgcct attgtagacg tcaacccgca tctggtgcga atatagcgca    240
cccccaatga tcacaccaac aattggtcca ccccctccca aaagctttag ttttcaacat    300
tttgtgctcc ccccgctgtt tgaaaacggg ggtgagcgct ctccggggtg cgaattcgtg    360
cccaattcct ttcaccctgc ctattgtaga cgtcaacccg catctggtgc gaatatagcg    420
cacccccaat gatcacacca acaattggtc caccctccc caatctctaa tattcacaat    480
tcacctcact ataaataccc ctgtcctgct cccaaattct ttttccttc ttccatcagc    540 tactagcttt tatcttattt actttacgaa a                                   571

<210> SEQ ID NO 51
<211> LENGTH: 753
<212> TYPE: DNA
<213> ORGANISM: Artificial Sequence
<220> FEATURE:
<223> OTHER INFORMATION: Synthetic promoter

<400> SEQUENCE: 51
atgcccggag gagacttgcc ccctaatttc gcggcgtcgt cccggatcgc agggtgagac    60
tgtagagacc ccacatagtg acaatgatta tgtaagaagt ctagatagtt ttcaacattt    120
tgtgctcccc ccgctgtttg aaaacggggg tgagcgctct ccggggtgcg aattcgtgcc    180
caattccttt caccctgcct attgtagacg tcaacccgca tctggtgcga atatagcgca    240

-continued

```
ccccaatga tcacaccaac aattggtcca ccctccccca agagctctag ttttcaacat    300
tttgtgctcc ccccgctgtt tgaaaacggg ggtgagcgct ctccggggtg cgaattcgtg    360
cccaattcct ttcaccctgc ctattgtaga cgtcaacccg catctggtgc gaatatagcg    420
cacccccaat gatcacacca acaattggtc caccctccc caaaagcttt agttttcaac    480
attttgtgct cccccgctg tttgaaaacg ggggtgagcg ctctccgggg tgcgaattcg    540
tgcccaattc ctttcaccct gcctattgta gacgtcaacc cgcatctggt gcgaatatag    600
cgcaccccca atgatcacac caacaattgg tccaccctc cccaatctct aatattcaca    660
attcacctca ctataaatac ccctgtcctg ctcccaaatt cttttttcct tcttccatca    720
gctactagct tttatcttat ttactttacg aaa                                753

<210> SEQ ID NO 52
<211> LENGTH: 1011
<212> TYPE: DNA
<213> ORGANISM: Artificial Sequence
<220> FEATURE:
<223> OTHER INFORMATION: Synthetic promoter

<400> SEQUENCE: 52
atgcccggag gagacttgcc ccctaatttc gcggcgtcgt cccggatcgc agggtgagac     60
tgtagagacc ccacatagtg acaatgatta tgtaagaaga gggggtgat tcggccggct    120 atcgaactct aacaactagg ggggtgaaca atgcccagca gtcctcccca ctctttgaca    180
aatcagtatc accgattaac accccaaatc ttattctcaa cggtccctca tccttgcacc    240
cctctttgga caaatggcag ttagcattgg tgcactgact gactgcccaa ccttaaaccc    300
aaatttctta aaggggccc atctagttag cgaggggtga aaaattcctc catcggagat    360
gtattgaccg taagttgctg cttaaaaaaa atcagttcag atagcgagac tttttttgatt    420 tcgcaacggg agtgcctgtt ccattcgatt gcaattctca ccccttctgc ccagtcctgc    480
caattgccca tgaatctgct aatttcgttg attcccaccc ccctttccaa ctccacaaat    540
ctagatagtt ttcaacattt tgtgctcccc ccgctgtttg aaaacggggg tgagcgctct    600
ccggggtgcg aattcgtgcc caattccttt caccctgcct attgtagacg tcaacccgca    660
tctggtgcga atatagcgca ccccaatga tcacaccaac aattggtcca ccctcccca    720 aaagctttag ttttcaacat tttgtgctcc ccccgctgtt tgaaaacggg ggtgagcgct    780
ctccggggtg cgaattcgtg cccaattcct ttcaccctgc ctattgtaga cgtcaacccg    840
catctggtgc gaatatagcg cacccccaat gatcacacca acaattggtc caccctccc    900 caatctctaa tattcacaat tcacctcact ataaatacc ctgtcctgct cccaaattct    960
tttttccttc ttccatcagc tactagcttt tatcttattt actttacgaa a             1011
```

DETERMINATION OF REGULATORY DNA REGIONS OF ALCOHOL DEHYDROGENASE 3 (ADH3) PROMOTER AND DESIGN OF SYNTHETIC PROMOTERS FOR RECOMBINANT PROTEIN PRODUCTION

INCORPORATION BY REFERENCE

The file entitled "17071-27 Sequence Listing.txt" is hereby incorporated by reference into the present application. This ASCII text file was created 2 Sep. 2021 to correct formatting. This file is 15,969 bytes (~16 KB) in size and contains no new matter.

TECHNICAL FIELD RELATED TO THE INVENTION

This invention relates to DNA regions responsible for the regulation of the alcohol dehydrogenase 3 (ADH3) promoter of *Pichia pastoris* (*Komagatella pastoris*), vectors and expression cassettes containing these DNA regions, and host cells comprising these vectors and expression cassettes. It also includes mutant ADH3 promoters that operate at different strengths that can be used in the production of recombinant protein.

STATE OF THE ART

The first choice in recombinant protein production is usually a prokaryotic expression system because it is easy and cheap. However, during the production of eukaryotic proteins in prokaryotic systems, problems may be encountered, such as the protein being unstable or not performing its biological activity. The intracellular environment of yeasts is more suitable for the production of eukaryotic proteins than prokaryotic systems. Yeasts as eukaryotic expression systems has ability to perform post-translational biochemical reactions (such as disulfide bond formation, glycosylation), which are essential for eukaryotic proteins.

*Saccharomyces cerevisiae* is the most widely used eukaryotic host due to its extensive knowledge of genetics and physiology. However, there are some disadvantages of using *S. cerevisiae* in recombinant protein production such as loss of plasmid in large-scale production, hyperglycosylation and low yield. Recently, as an alternative to *S. cerevisiae*, a methylotrophic yeast *Pichia pastoris* (*Komagataella pastoris, K. phaffi, K. pseudopastoris*) was developed. In literature, there are different sources which *P. pastoris* called as *Komagataella pastoris, K. phaffi, K. pseudopastoris*. Here, it was referred to as *P. pastoris*. *P. pastoris* yeast as a eukaryotic microorganism has the advantages of *S. cerevisiae* in terms of molecular and genetic manipulations, but it is a more efficient host system than *S. cerevisiae*. *P. pastoris* is an excellent host for the production of recombinant proteins, particularly in the industrial field.

The most commonly used promoter for recombinant protein production with *P. pastoris* is methanol-inducible AOX1 promoter. *P. pastoris*, a methylotrophic yeast, requires high levels of enzymes such as alcohol oxidase during its development in methanol media. In the *P. pastoris* genome, the alcohol oxidase gene is present in two copies: AOX1 and AOX2. While AOX1 is responsible for 85% of alcohol oxidase activity, AOX2 is responsible for 15%. The highest expression level in recombinant protein production with *P. pastoris* (22 g/L in intracellular production, up to 15 g/L in extracellular production) was achieved with $P_{AOX1}$. In addition, a constitutive $P_{GAP}$ (glyceraldehyde 3-phosphate dehydrogenase) is also commonly used promoter in *P. pastoris*. However, its use is not as common as $P_{AOX1}$ as it is not suitable for the production of foreign proteins which are toxic to the cell.

Alternative *P. pastoris* promoters and expression levels are summarized in Table 1. The approximate expression levels of these promoters were compared with the $P_{GAP}$ and $P_{AOX1}$ expression levels. The expression levels measured in different culture conditions are given in intervals.

TABLE 1

Alternative *P. pastoris* promoters and expression levels (Yogi and Glieder, 2013)

| Gene name | Gene product | Regulation | Expression level |
|---|---|---|---|
| AOX1 | Alcohol oxidase 1 | Induced by methanol | Strong (naturally 5% of mRNA and 30% of total protein) |
| GAP | Glyceraldehyde 3-phosphate dehydrogenase | Constitutive | Strong (similar to $P_{AOX1}$) |
| AOX2 | Alcohol oxidase 2 | Induced by methanol | 5-10% of $P_{AOX1}$ |
| DAS | Dihydroxyacetone synthase) | Induced by methanol | Strong (similar to $P_{AOX1}$) |
| ENO1 | Enolase | Constitutive | 20-70% of $P_{GAP}$ |
| FLD1 | Formaldehyde dehydrogenase | Induced by methanol and methylamine | Strong (similar to $P_{AOX1}$) |
| GPM1 | Phosphoglycerate mutase | Constitutive | 15-40% of $P_{GAP}$ |
| PET9 | ADP/ATP carrier of the inner mitochondrial membrane | Constitutive | 10-1700% of $P_{GAP}$ |
| PEX8 | Peroxisomal matrix protein | Induced by methanol or oleate | Weak |
| TEF1 | Translation elongation factor 1 alpha | Constitutive | Strong (similar to $P_{GAP}$) |
| THI11 | Protein involved in thiamine biosynthesis | Completely repressed by thiamine | 70% of $P_{GAP}$ on medium lacking thiamin |

Studies on using *P. pastoris* expression system more effectively and efficiently are ongoing. Genetic modifications, in natural promoters and development of existing promoters for the purpose of use are among these studies. Thus, expression of a foreign protein can be increased or decreased as desired using the related promoters.

Patents related to the regulation of the AOX1 promoter, which is commonly used in the production of recombinant protein with *P. pastoris* are available. Refer. U.S. Pat. Nos. 6,699,691 and 9,012,175.

The subject of this invention is *P. pastoris* ADH3 promoter. Although there is a patent on protein expression with this promoter, sec. U.S. Pat. No. 8,222,386, there is no experimental data on DNA regions involved in the regulation of the promoter and the shortest DNA sequence in which ADH3 promoter activity is maintained at 100%. In addition, the patent mentioned does not provide the absolute expression level of the ADH3 promoter. In our previous studies, recombinant protein production in *P. pastoris* with ADH3 promoter was compared with the most commonly used *P. pastoris* promoters AOX1 and GAP. The results showed that in the production of recombinant proteins under fermenter conditions, the specific productivity of the ADH3 promoter was 1.3 times the AOX1 promoter (Karaoglan et al. 2016a).

There ae differences in the nomenclature of ADH3 gene in the literature. Genome sequences of *P. pastoris* GS115 and *P. pastoris* DSMZ 70382 strains were recently discovered and one gene encoding alcohol dehydrogenase enzyme was identified (De Schutter et al. 2009; Mattanovich et al. 2009). The same gene sequence was referred to as the ADH1 gene in the aforementioned patent (U.S. Pat. No. 8,222,386) and the promoter region responsible for the regulation of this gene in the same patent was referred to as ADH1 promoter (Cregg and Tolstorukov 2008), and, referred to as ADH2 in second genome study (DSMZ 70382 strain) (Mattanovich et al. 2009). However, in the NCBI database, this gene was identified and named ADH3 in *P. pastoris* (strain GS115) because of the similarity to ADH3 amino acid sequence of *S. cerevisiae* (De Schutter et al. 2009). The ADH3 gene has been characterized by our previous studies and has been shown to be the only gene responsible for ethanol consumption in *P. pastoris* ethanol metabolism (Karaoglan et al. 2016b). All the genes mentioned above have the same gene sequence. In our previous work and in the present invention, it has been referred to as the ADH3 promoter based on the database naming.

PURPOSE OF THE INVENTION

The invention relates to *P. pastoris* ADH3 promoter. The main purpose of the invention is to improve the properties of *P. pastoris* ADH3 promoter. In this way, protein production can be performed more efficiently. In order for the invention to fulfill this purpose, it is necessary to determine the regions (e.g., regulatory regions and transcription factor binding sites) that play a role in the regulation on the ADH3 promoter (SEQ ID NO: 1). The other purpose depending on the determination of regulator regions is to provide tools for the creation of new synthetic promoters.

DESCRIPTION OF FIGURES

The method and advantages of the invention will be better understood by means of the figures and their descriptions.

DESCRIPTION OF THE REFERENCES

Figure 1A:
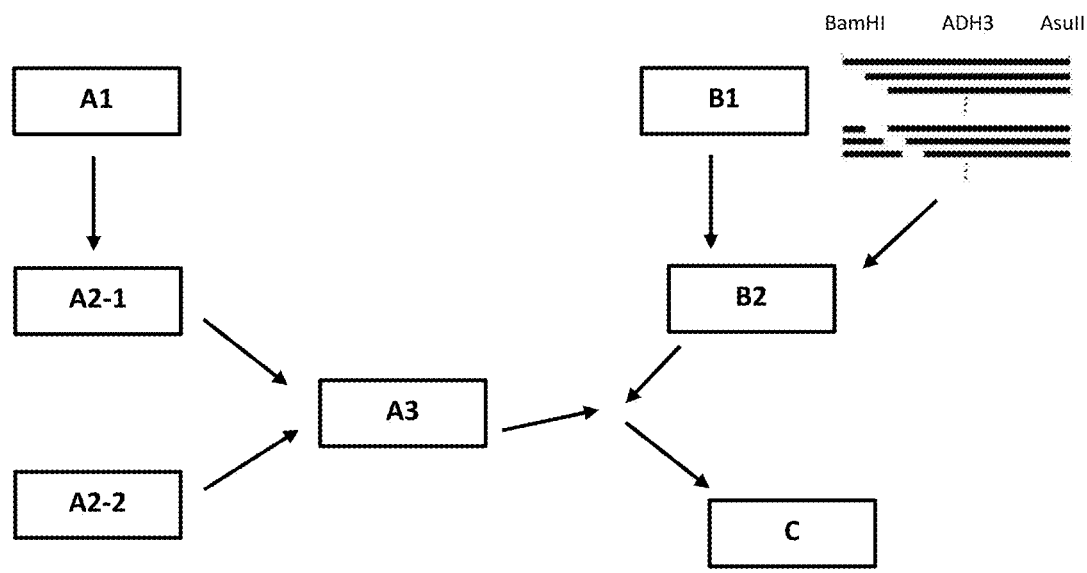
FIG. 1: The construction steps of expression vectors (cassettes) pADH3ZαA-XylB/HIS4 (A. schematic illustration of construction steps with plasmids, B. A1 plasmid, C. A2-1 plasmid, D. A2-2 plasmid, E. A3 plasmid, F. B1 plasmid, G. B2 plasmid, H. C plasmid)
Figure 1B:
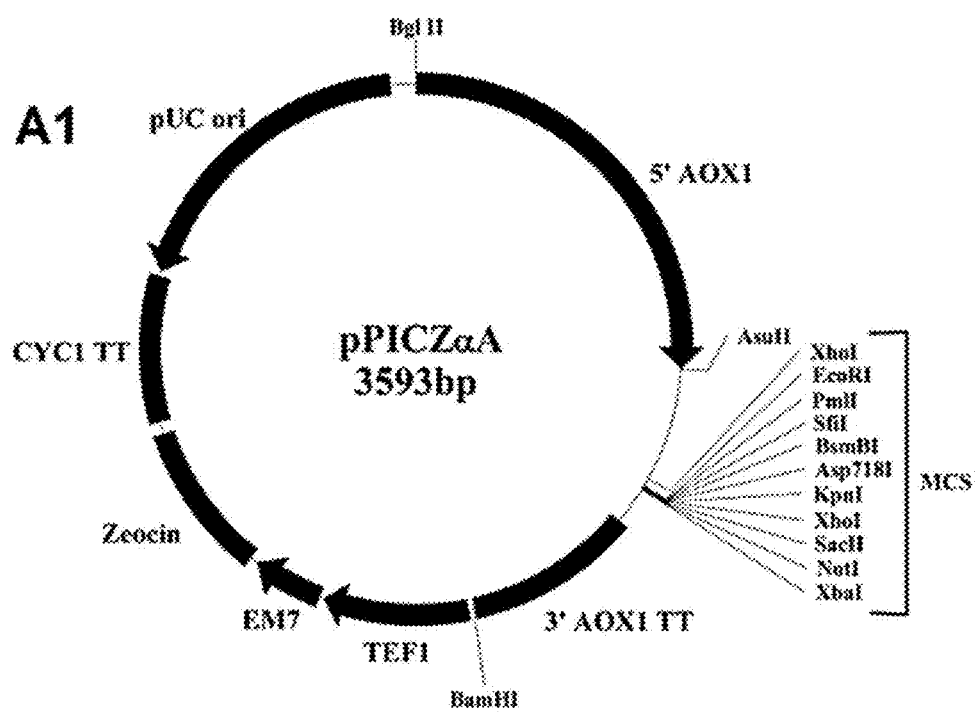
Figure 1C:
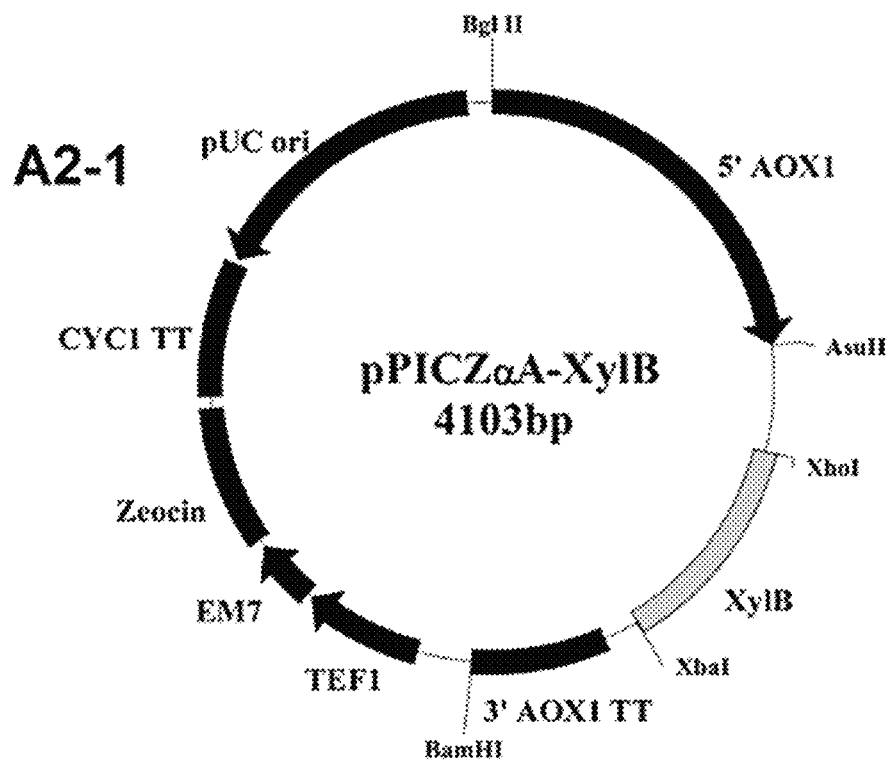
Figure 1D:
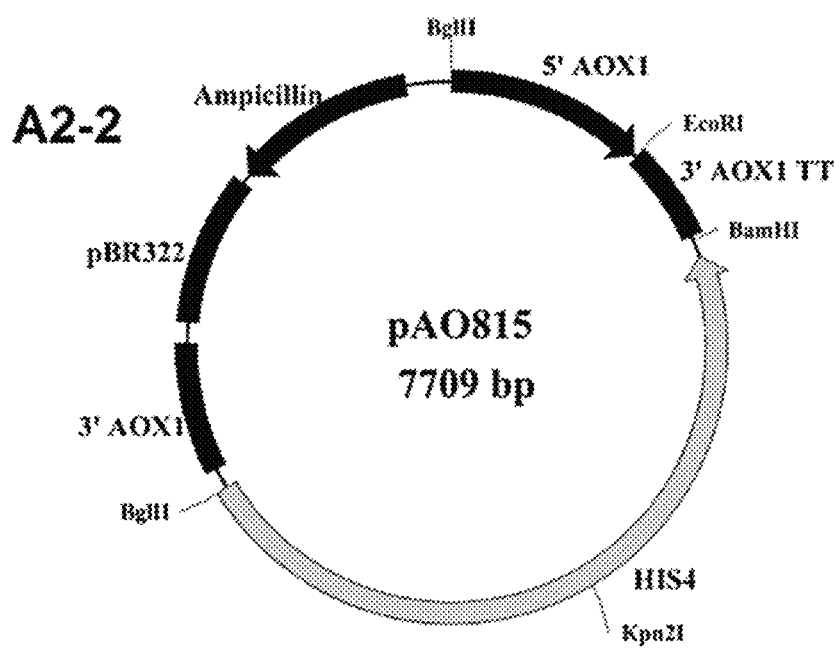
Figure 1E:
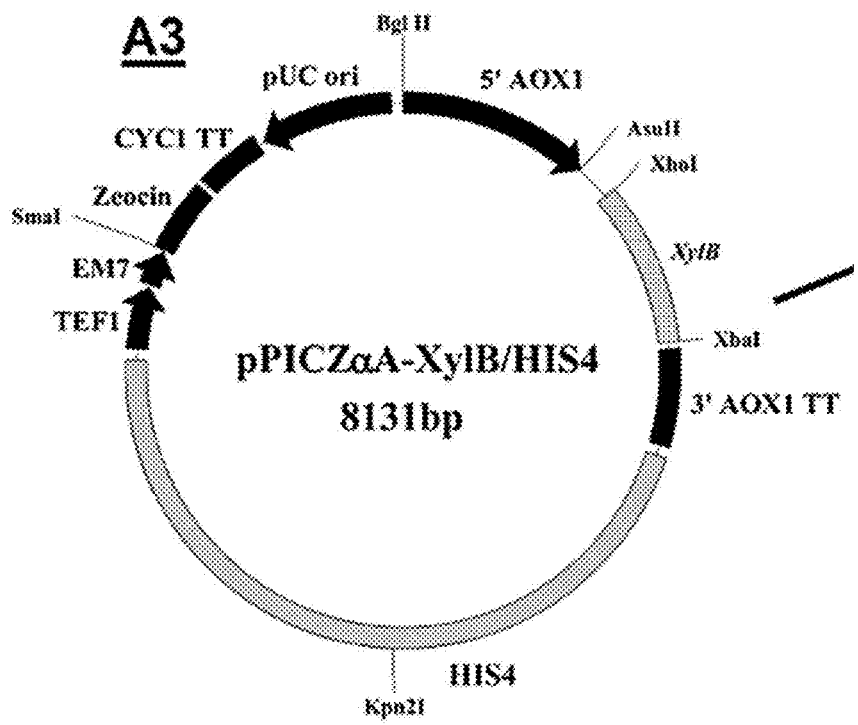
Figure 1F:
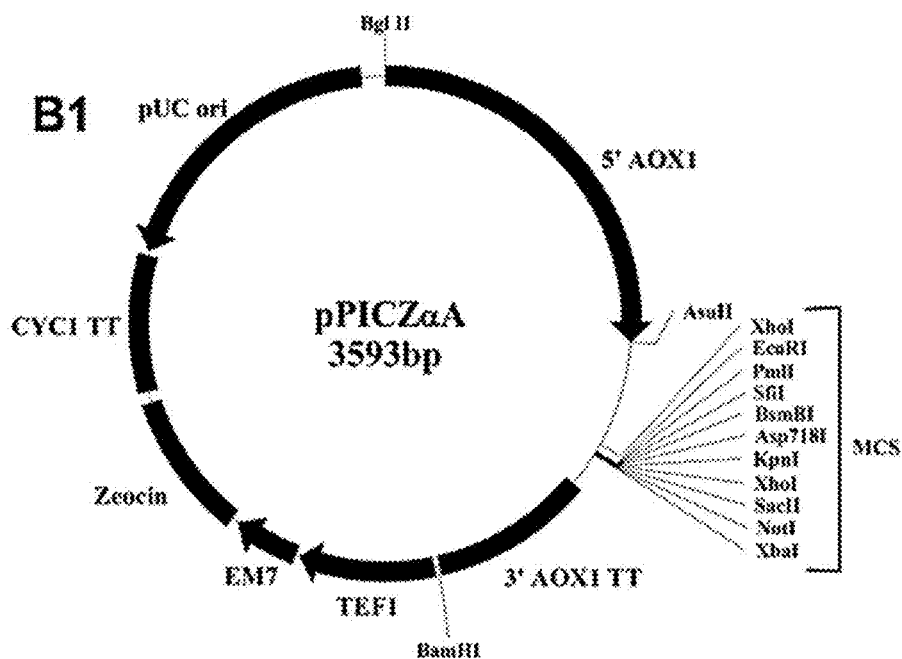
Figure 1G:
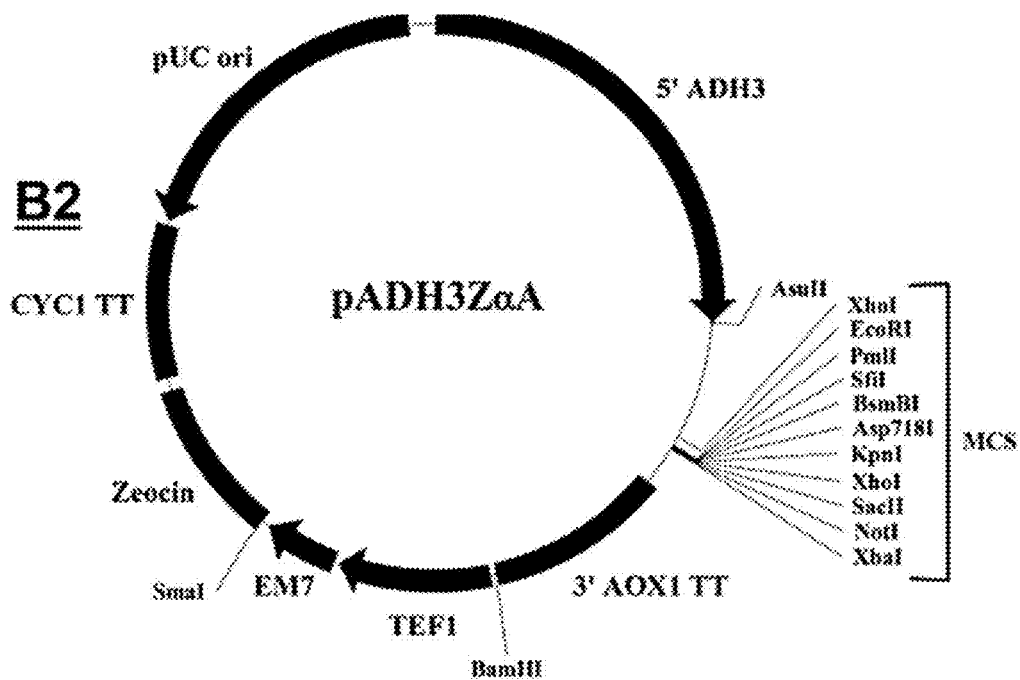
Figure 1H:
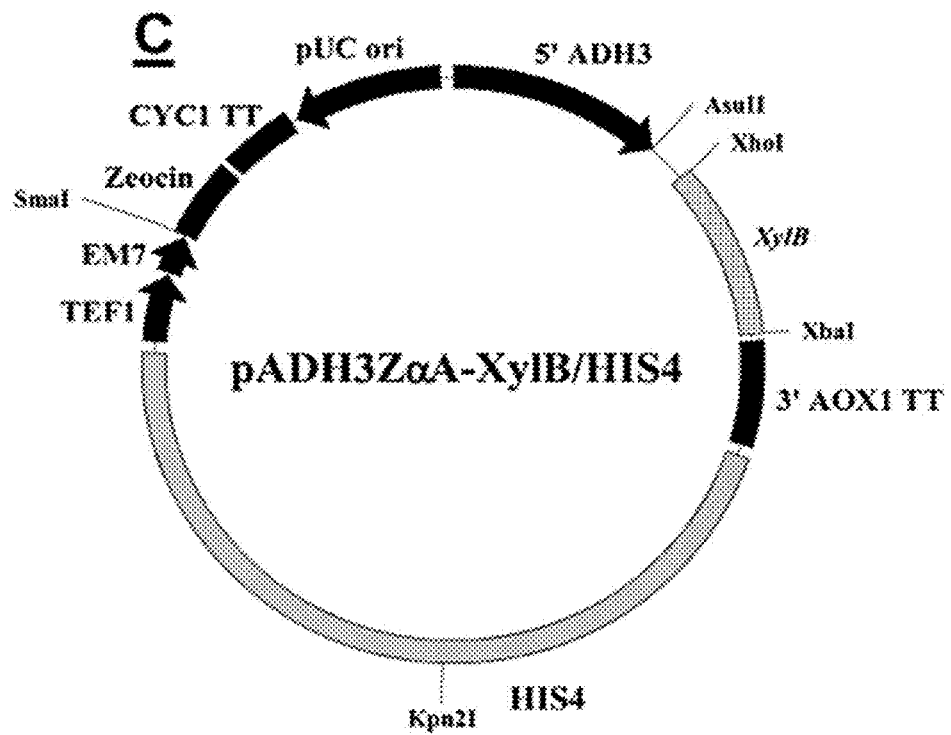
Figure 2:
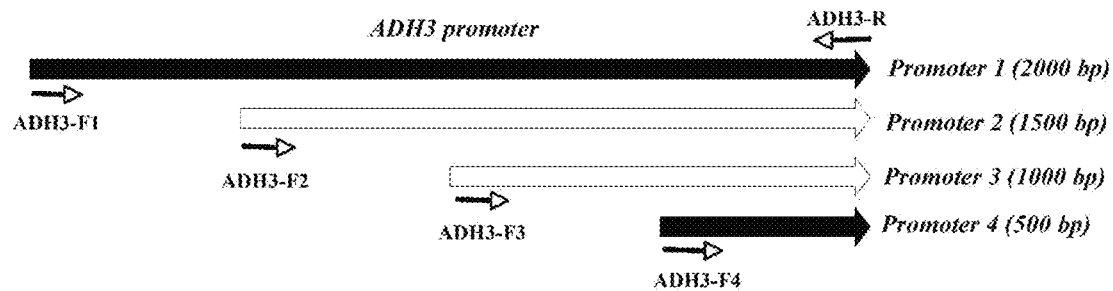
FIG. 2: Schematic representation of ADH3 promoter regions of different lengths
Figure 3:
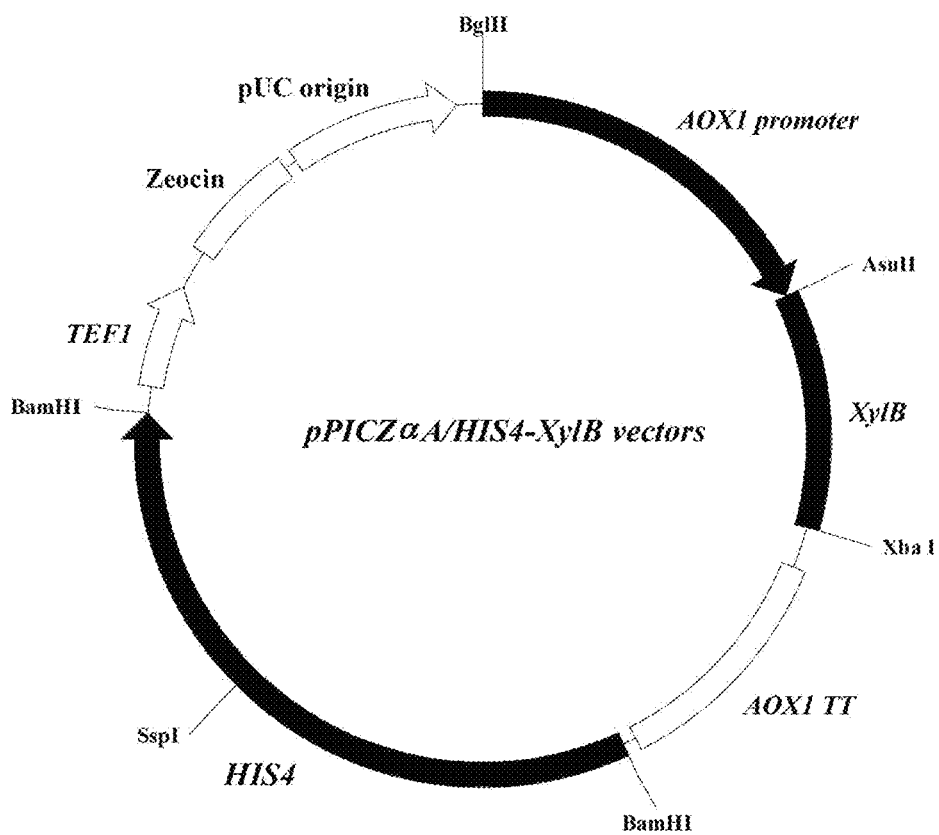
FIG. 3: Schematic representation of the vector pPICZαA/HIS4-XylB.
Figure 4:
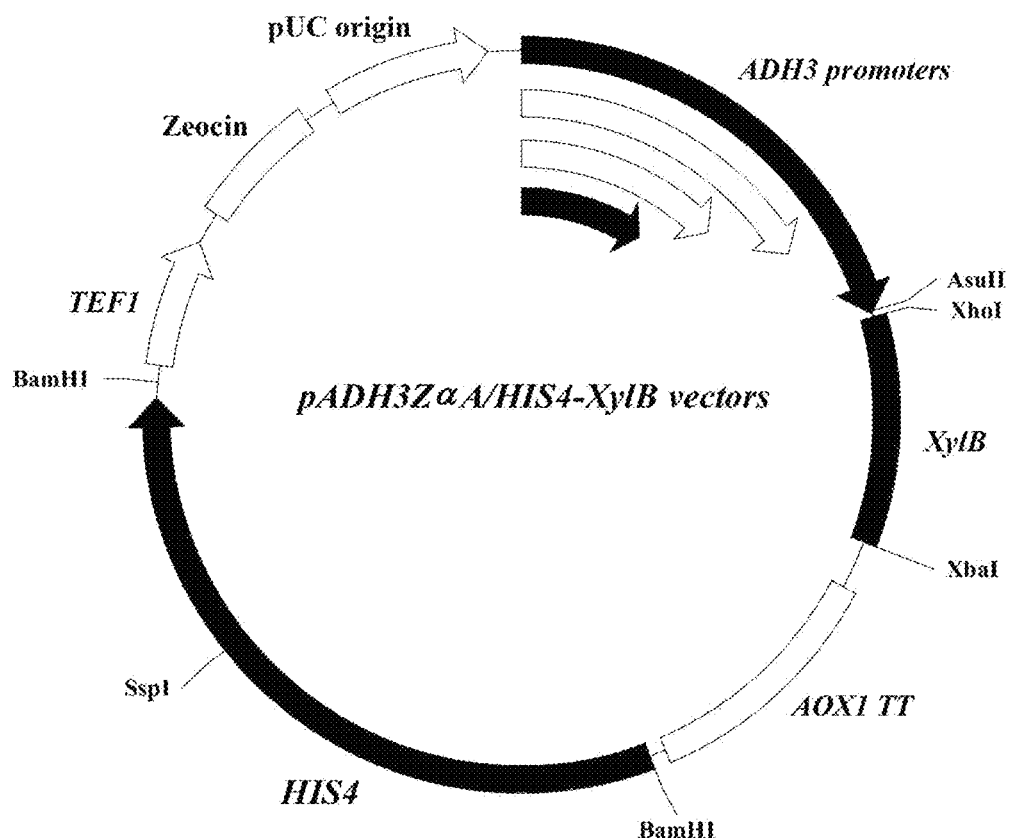
FIG. 4: Schematic representation of the vectors obtained by replacing the AOX1 promoters with the ADH3 promoters in the plasmid pPICZαA/HIS4-XylB.

A1: First construction step of expression vector pPICZαA-XylB/HIS4 with A1 plasmid A2-1: Second construction step of expression vector pPICZαA-XylB/HIS4 with A2-1 plasmid A2-2: Second construction step of expression vector pPICZαA-XylB/HIS4 with A2-2 plasmid A3: Third construction step of expression vector pPICZαA-XylB/HIS4 with A3 plasmid B1: First construction step of expression vector pADH3ZαA with B1 plasmid B2: Second construction step of expression vector pADH3ZαA with B2 plasmid C: Expression vector pADH3ZαA-XylB/HIS4 as C plasmid

DESCRIPTION OF THE INVENTION

The invention relates to the method of expression of a recombinant protein, peptide or functional nucleic acid in a cell, determination of DNA regions responsible for regulation of alcohol dehydrogenase 3 (ADH3) promoter and design of synthetic promoters for recombinant protein production.

Within the scope of the invention, ADH3 promoter region was determined as the shortest DNA sequence in which ADH3 promoter activity was maintained at 100% and 5' end- and internal deletion analyzes were performed on this region determined. The results showed the effects of these regions on promoter activity. Also, synthetic promoters were constructed using the DNA regions known to be effective on promoter activity. It is also possible to form new synthetic promoters of different strengths using the data presented in the present invention.

The general method of expression of a recombinant protein, peptide or functional nucleic acid in the cell is as follows; determination of ADH3 promoter to be selected, operably linking promoter to nucleic acid molecule encoding of a protein, peptide or functional nucleic acid and transforming the host cell with vector or the nucleic acid molecule, growth of the transformed host cell under suitable culture conditions, inducing expression of this protein, peptide or functional nucleic acid, and isolation of this protein, peptide or functional nucleic acid.

In the following description for the method according to the invention, the (negative) numbers shown in brackets indicate their position relative to the translation initiation codon of the promoter.

1. Determination of the ADH3 Promoter

In order to determine the regions involved in the regulation of the ADH3 promoter (e.g., regulatory regions and transcription factor binding sites), it is first necessary to determine the promoter region of the ADH3.

To determine the ADH3 promoter, the 2000 bp DNA region at the 5' end of the ADH3 gene was examined and divided into four regions.

The shortest DNA region in which ADH3 promoter activity maintained at 100% was determined.

In order to identify the promoter region precisely, 5' end-deletion analyzes were performed on the shortest DNA region determined in the previous stage.

The results of 5' end-deletion analysis, the increases and decreases observed in the promoter activity, can provide clues about the regulatory regions.

In the first step of the method for obtaining the mutant promoters of the invention, to identify the ADH3 promoter; The 2000 bp DNA region at the 5 'end of the ADH3 gene was examined as the regions of 2000 (Nucleotide −2000 to 0), 1500 (Nucleotide −1500 to 0), 1000 (Nucleotides −1000 to 0) and 500 (Nucleotide −500 to 0) bp. The shortest DNA region in which the activity of the ADH3 promoter was maintained at 100% was determined to be 1000 bp (Nucleotide −1000 to 0). Then, in order to identify the promoter region precisely, 5' end-deletion analysis was applied to 1000 bp promoter region and it was serially truncated 100 bp from the 5' upstream region.

Figure 6:
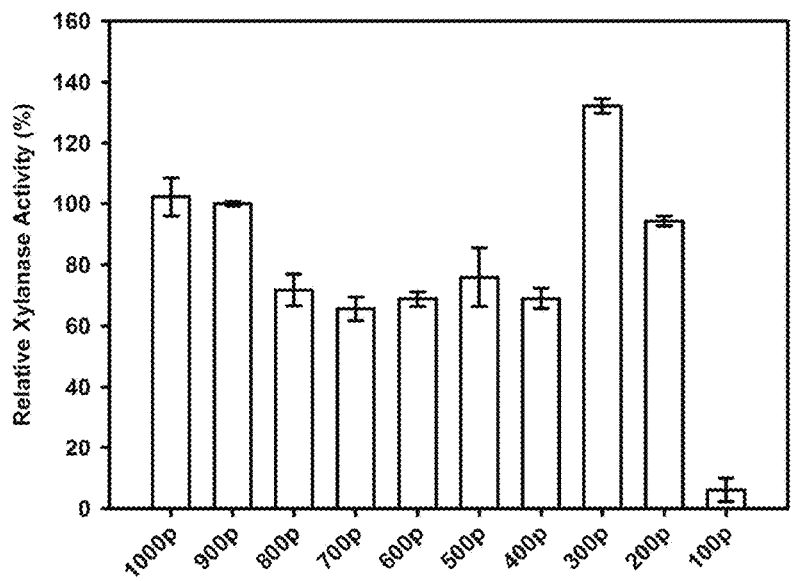
FIG. 6: Graphical representation of the promoter activities obtained by 5' end-deletion analysis of the ADH3 promoter.

5' end-deletion analysis: To determine the exact length of the ADH3 promoter, the 1000 bp promoter was serially truncated 100 bp from the 5' end. The promoter regions thus obtained were the DNA regions between −900 to 0, −800 to 0, −700 to 0, −600 to 0, −25 to 500 to 0, −400 to 0, −300 to 0, −200 to 0, −100 to 0 nucleotides. Among the obtained promoters, the shortest DNA region in which activity was unchanged, i.e. the exact promoter region, was determined to be 900 bp (Nucleotide −900 to 0) and this region was identified as ADH3 promoter (SEQ ID NO:1). The promoter activities obtained by 5' end-deletion analysis were given graphically in FIG. 6.

2. Determination of Regulatory DNA Regions in the ADH3 Promoter

To more accurately identify the DNA regions responsible for regulation in the ADH3 promoter, internal deletion analysis was performed on 900 bp promoter (Sequence ID NO: 1).

The regions deleted were the nucleotides between 0 to 99 (−900 to −801), 77 to 176 (−823 to −724), 154 to 253 (−746 to −647), 231 to 330 (−669 to −570), 308 to 407 (−592 to −493), 385 to 484 (−515 to −416), 462 to 561 (−438 to −339), 539 to 638 (−361 to −262), 616 to 715 (−284 to −185), 693 to 792 (−207 to −108), 770 to 814 (−130 to −86) and 200 to 500 (−700 to −400).

Figure 7:
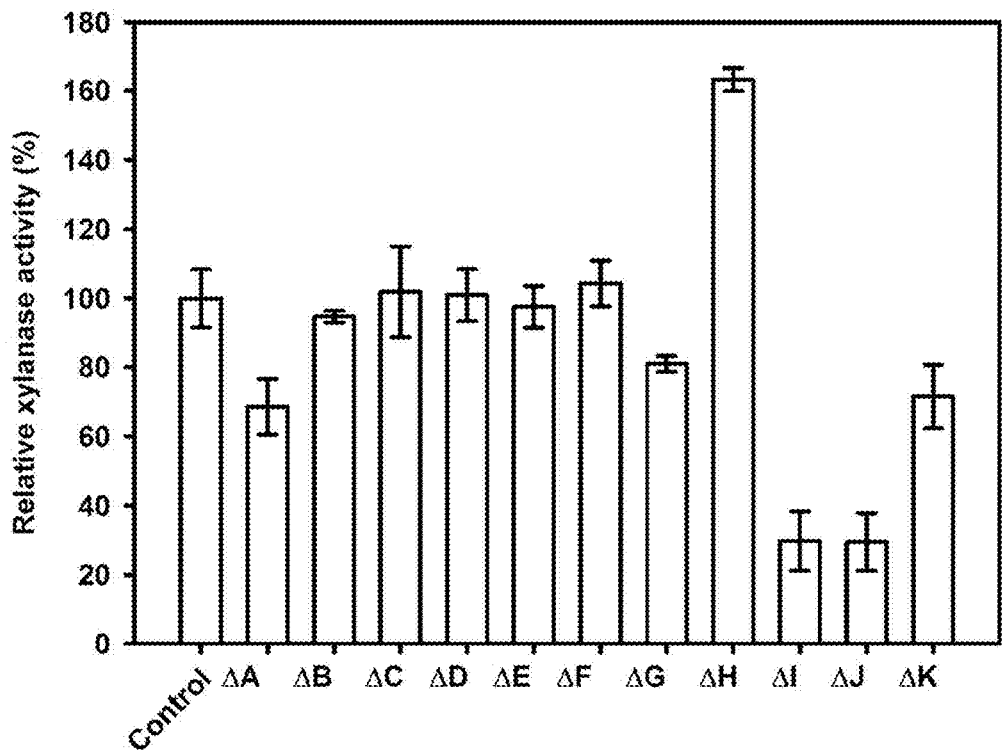
FIG. 7: Graphical representation of the promoter activities obtained by internal deletion analysis of the ADH3 promoter.

The promoter activities obtained by internal deletion analysis were given graphically in FIG. 7.

According to the present invention, the mutations between the nucleotides 0 to 99 (−900 to −801), 462 to 561 (−438 to −339), 539 to 638 (−361 to −262), 616 to 715 (−284 to −185), 693 to 792 (−207 to −108) and 770 to 814 (−130 to −86) on SEQ ID NO:1 were determined to be effective in the regulation of the ADH3 promoter in terms of positive or negative regulation under the ethanol-induced conditions.

Also, it was determined that the mutations between 77 to 176 (−823 to −724), 154 to 253 (−746 to −647), 231 to 330 (−669 to −570), 308 to 407 (−592 to −493), 385 to 484 (−515 to −416) and 200 to 500 (−700 to −400) nucleotides on SEQ ID NO: 1 and the combinations of these mutations had no significant effect on the promoter activity.

The protein expression yield of the synthetic promoter sequences may vary depending on the number of expression cassettes integrated into the host cell genome. In particular, there was an increase in promoter activity in strains containing more than one copy expression cassette. The clone in which the expression cassette, containing the DNA region from 500 to 900 (−400 to 0) nucleotides on ADH3 promoter (SEQ ID NO:1) as a promoter, was integrated in 2 copies, showed an increase in protein production relative to the single copy clone.

3. Design of Synthetic Promoters Using the Promoter Regions that Affect the Strength of the ADH3 Promoter The data on promoter regions that affect the strength of the ADH3 promoter can be used to design promoters with different characteristics. The promoters obtained according to the preferred embodiment of the present invention are used in a yeast cell, preferably a methylotrophic yeast cell. These methylotrophic yeast cells can be *Pichia*, especially *P. pastoris, Candida, Hansenula* and *Torulopsis* cells. As in an example, previous studies have shown that the oxygen-regulated ADH promoter of *P. stipitis* was regulated in the same manner in *P. pastoris* yeast (Chien and Lee, 2005).

3a. Construction of Expression Vectors (Cassettes)

The construction steps of expression cassettes were shown in FIG. 1.

The construction steps of expression vector pPICZαA-XylB/HIS4 were schematized by line A (A1, A2-1, A2-2 and A3).

The construction steps of expression vector pADH3ZαA were schematized by line B (B1 and B2).

The expression vector obtained from line A, pPICZαA-XylB/HIS4 and the expression vector obtained from line B, pADH3ZαA were combined and the expression vector pADH3ZαA-XylB/HIS4 schematized by line C was obtained.

The native ADH3 promoter regions of different lengths were amplified by PCR using the forward primer containing BamHI restriction site and the reverse primer containing AsuII restriction. PCR analyzes were performed using KOD Hot Start DNA Polymerase Kit according to the manufacturer's instructions. Mutant ADH3 promoter regions were obtained using overlap PCR method. The primers used in PCR reactions and the ADH3 promoter regions obtained were given in Table 2.

TABLE 2

Primer list (Macrogen Inc., Seoul, South Korea)

| SEQ ID No: | Name | Melting Temperature [° C.] |
|---|---|---|
| 2 | 1000p-F | 75.0 |
| 3 | 900p-F | 74.7 |
| 4 | 800p-F | 74.2 |
| 5 | 700p-F | 66.2 |
| 6 | 600p-F | 69.0 |
| 7 | 500p-F | 72.0 |
| 8 | 400p-F | 69.0 |
| 9 | 300p-F | 67.6 |
| 10 | 200p-F | 70.4 |
| 11 | 100p-F | 66.2 |
| 12 | ADH3-R | 63.0 |
| 13 | ADH3F -801 | 74.4 |
| 14 | ADH3R -823 | 75.5 |
| 15 | ADH3F -724 | 75.5 |
| 16 | ADH3R -746 | 76.6 |
| 17 | ADH3F -647 | 76.6 |
| 18 | ADH3R -669 | 76.6 |
| 19 | ADH3F -570 | 76.6 |
| 20 | ADH3R -592 | 69.8 |
| 21 | ADH3F -493 | 69.8 |
| 22 | ADH3R -515 | 74.4 |
| 23 | ADH3F -416 | 74.4 |
| 24 | ADH3R -438 | 75.5 |
| 25 | ADH3F -339 | 75.5 |
| 26 | ADH3R -361 | 76.6 |
| 27 | ADH3F -262 | 76.6 |
| 28 | ADH3R -284 | 76.6 |
| 29 | ADH3F -185 | 76.6 |
| 30 | ADH3R -207 | 73.2 |
| 31 | ADH3F -108 | 73.2 |

TABLE 2-continued

Primer list (Macrogen Inc., Seoul, South Korea)

| SEQ ID No: | Name | Melting Temperature [° C.] |
|---|---|---|
| 32 | ADH3R -130 | 74.4 |
| 33 | ADH3F -86 | 74.4 |
| 34 | ADH3R -700 | 72.1 |
| 35 | ADH3F -400 | 72.1 |

The construction steps (A1, A2-1, A2-2 and A3) of expression vector pPICZαA-XylB/HIS4 given in line A;

Plasmid A1 shown in FIG. 1, the commercial pPICZαA, was ligated to the reporter XylB gene from the XhoI-XbaI cloning site to obtain A2-1 and was named pPICZαA-XylB.

Plasmid A2-2, commercial pAO815, was used to obtain the HIS4 gene used as marker. The HIS4 gene obtained by cutting with BglII-BamHI was ligated to the pPICZαA-XylB which was linearized with BamHI to obtain the A3 plasmid and was named pPICZαA-XylB/HIS4.

The construction steps (B1 and B2) of expression vector pADH3ZαA given in line B;

B1, the commercial pPICZαA, was digested with BglII-AsuII to excise the AOX1 promoter. The new promoterless construct was ligated to the PCR products of different ADH3 promoters digested with BamHI-AsuII and B2 was obtained. The plasmid B2 is named pADH3ZαA.

Ligation of pPICZαA-XylB/HIS4 obtained from line A and pADH3ZαA obtained from line B to obtain pADH3ZαA-XylB/HIS4 shown in line C pPICZαA-XylB/HIS4 (A3) and pADH3ZαA (B2) plasmids were ligated from the XhoI-SmaI restriction site. The ligated fragments are the portion containing ADH3 promoter in pADH3ZαA and the portion containing the XylB and HIS4 genes in pPICZαA-XylB/HIS4 plasmids that were obtained by XhoI-SmaI digestion reactions of both plasmids. The final plasmid was named pADH3ZαA-XylB/HIS4.

3b. Transformation (Integration) of Expression Vectors into Host Cell Genome

All ADH3 expression plasmids of the invention were generated by the same strategy. Plasmids were linearized with Kpn2I and integrated into the host cell genome from the his4 locus. *P. pastoris* GS115 was used as the host cell.

The integrated host cells were grown in appropriate culture conditions to produce xylanase enzyme (reporter protein) under the control of promoters constructed within the scope of the invention.

It is possible to carry out different protein productions in different yeast cells using mutant ADH3 promoters and novel mutant promoters which can be formed as addition, deletion, substitution and inversion of the promoter regions of ADH3.

An example of the use of the invention in methylotrophic yeast cells is given in Example 1 for use in the *P. pastoris* cell.

Example 1

Material and Methods
Strains, Plasmids and Media

*P. pastoris* strains used in studies were X33 (Wild-type) and GS115 (his4, Invitrogen). The media used for *P. pastoris*: YPD (1% yeast extract, 2% peptone, 2% glucose), MG (1.34% YNB, $4\times10^{-5}$% biotin and 2% glycerol) and ME (1.34% YNB, $4\times10^{-5}$%). biotin and 1% ethanol), BMGY (2% peptone, 1% yeast extract, 1.34% YNB, $4\times10^{-5}$% biotin and 2% glycerol) and BMEY (2% peptone, 1% yeast extract, 1.34% YNB, $4\times10\%^{-5}$ biotin and 1% ethanol).

As the expression vector for the recombinant protein production, pADH3ZαA-XylB/HIS4, the plasmid containing the native and mutant ADH3 promoters, constructed in accordance with the invention was used. *Aspergillus niger* xylanase gene (XylB) was used as the reporter gene. *Escherichia coli* XL1-Blue strain was used for cloning and propagation of plasmids. LB medium (0.5% yeast extract, 1% peptone and 1% NaCl) was prepared with appropriate antibiotic additions to grow *E. coli* cells.

General Molecular Biology Techniques

The restriction endonucleases and their buffer solutions were obtained from Fermentas (MD, USA). DNAMAN 7.0 (Lynnon Corporation) was used for all primer designs and DNA analyzes. Primers were obtained from Macrogen Inc. (Seoul, South Korea). The National Biotechnology Information Center Network Service (Bethesda, Md., USA; http://www.ncbi.nlm.nlh.gov) was used for screening of gene and protein sequences. Molecular cloning techniques were performed in accordance with Sambrook and Russel (2001) and kit protocols. Southern blot method was used for the confirmation of the integration of the expression cassette into the genome and the determination of clones containing a single copy expression cassette. In the Southern blot analysis, 527 bp HIS4 fragment which was amplified by PCR from plasmid pPIC3.5K and labeled with digoxigenin (DIG) was used as probe.

Determination of Xylanase Enzyme Activity

Xylanase activity was determined by measuring the reducing sugar released from the xylan (Miller 1959). The supernatant sample (0.1 mL) was added to 0.9 mL of 0.05 M sodium citric acid buffer (pH 5.00) containing 1% (w/v) beechwood xylan. The reaction mixture was incubated at 50° C. for 5 minutes. At the end of the incubation period, 100 µl of the reaction mixture was added into the 900 µl of DNSA to stop the reaction. The mixture was incubated at boiling water bath for 5 minutes and after cooling, absorbance values were recorded spectrophotometrically at a wavelength of 540 nm. The amount of reducing sugar was determined by the dinitrosalicylic acid (DNSA) method. The blank samples were prepared by stopping the reaction with DNSA solution immediately after the enzyme was added to the substrate. One unit of xylanase activity was defined as the amount of enzyme needed to produce 1 µmol of reducing sugar (equivalent to glucose) under experimental conditions at 1 minute. The standard curve was plotted with 1-10 µmol xylose.

Results
Determination of ADH3 Promoter Region

Expression vectors containing the DNA regions of the 2000, 1500, 1000 and 500 bp in the 5' upstream portion of the ADH3 gene as promoters were integrated into the genome of the *P. pastoris* GS115 strain from his4 locus. Transformants containing a single copy expression cassette were selected and their copy number confirmed by Southern blot analysis (result not shown here). The transformants were inoculated into the medium containing glycerol and grown at 28° C. on a shaker for about 16 hours. The grown cells were transferred to the ethanol medium at the equal optical densities, and the supernatants were collected at the 8th hour of incubation. Activities of different length promoters were determined indirectly by measuring xylanase activity in supernatants. The results were determined relatively by normalizing the promoter activities to that of 2000 bp promoter defined as 100%. There was no difference in the tendency of promoter activities between minimal and rich media. The shortest DNA region in which the ADH3 promoter activity maintained unchanged was determined to be 1000 bp between the promoters 2000, 1500, 1000 and 500 bp (data not shown).

For a more accurate analysis of the promoter region, 1000 bp DNA region of the ADH3 promoter was serially truncated 100 bp from the 5' end and deletion analysis was continued to 100 bp DNA region. The results showed that the shortest DNA region in which the ADH3 promoter activity was 100% continued to be 900 bp and the ADH3 promoter region for further studies was determined as 900 bp (SEQ ID No: 1). The deletion of the region of −900 to −800 on the SEQ ID No: 1 caused a 30% reduction in promoter activity. This result can be expressed as the maintenance of 70% of the promoter activity with 800 bp promoter (Nucleotides −800 to 0). The promoter activity was maintained at about 70% in the DNA regions of 700 (nucleotide −700 to 0), 600 (nucleotide −600 to 0), 500 (nucleotide −500 to 0) and 400 (nucleotide −400 to 0). This means that 5' end-deletion analysis between −800 and −400 did not have an effect of increasing or decreasing the promoter activity. The promoter activity was approximately 130% with a 300 bp promoter (Nucleotide −300 to 0), and approximately 95% with a 200 bp promoter (Nucleotide −200 to 0) and about 6% with a 100 bp promoter (Nucleotide −100 to 0). Deletion of the repressor region results in an increase in promoter activity, while deletion of the activator region causes a decrease in promoter activity. The results showed that the promoter activity is 70% with 400 bp promoter and 130% with 300 bp promoter showed that there may have been a repressor region between −400 and −300 nucleotides. Promoter activity of the 200 bp region (Nucleotide −200 to 0) was obtained 95%, but this was a significant decrease in activity relative to the 300 bp promoter. This indicated that the activator sites could be located in a region between the nucleotides −300 and −200. Increases and decreases in promoter activity during 5' end-deletion can give some idea about regulator regions, but internal deletion analysis is required to obtain more accurate results.

Mutant ADH3 Promoters

Internal deletion analyzes (SEQ ID No: 1) were performed by overlap PCR method. The resulting mutant ADH3 promoters were ligated to expression vectors. The linearized plasmids were then integrated into the P. pastoris GS115 his4 locus. Transformants containing a single copy expression cassette were selected and their copy number was confirmed by Southern blot analysis (data not shown).

In the expression studies, the transformants were inoculated into the medium containing glycerol and grown at 28° C. for about 16 hours in the shaker. The grown cells were transferred to medium containing ethanol with equal optical density. The supernatants were collected at the 8th hour of incubation. Activities of the mutant ADH3 promoters were determined by measuring xylanase activity in the supernatants. The results were determined relatively by normalizing the promoter activities to that of 900 bp promoter defined as 100%.

Deleted regions in ADH3 promoter structures was given in Table 3. Deleted regions: Nucleotides 0 to 99 (−900 to −801), 77 to 176 (−823 to −724), 154 to 253 (−746 to −647), 231 to 330 (−669 to −570), 308 to 407 (−592 to −493), 385 to 484 (−515 to −416), 462 to 561 (−438 to −339), 539 to 638 (−361 to −262), 616 to 715 (−284 to −185), 693 to 792 (−207 to −108), 770 to 814 (−130 to −86) and 200 to 500 (−700 to −400).

TABLE 3

Deleted sequences in ADH3 promoter structures

| Construct | Position* 5' | Position* 3' | SEQ ID No: |
|---|---|---|---|
| ΔA | −900 | −801 | 36 |
| ΔB | −823 | −724 | 37 |
| ΔC | −746 | −647 | 38 |
| ΔD | −669 | −570 | 39 |
| ΔE | −592 | −493 | 40 |
| ΔF | −515 | −416 | 41 |
| ΔG | −438 | −339 | 42 |
| ΔH | −361 | −262 | 43 |
| ΔI | −284 | −185 | 44 |
| ΔJ | −207 | −108 | 45 |
| ΔK | −130 | −86 | 46 |
| Δ700-400 | −700 | −400 | 47 |

*The positions were given according to SEQ ID No: 1

According to the present invention, mutations between the nucleotides from 0 to 99 (−900 to −801), 462 to 561 (−438 to −339), 539 to 638 (−361 to −262), 616 to 715 (−284 to −185), 693 to 792 (−207 to −108) and 770 to 814 (−130 to −86) on SEQ ID NO: 1 have been found to be effective in the regulation of the ADH3 promoter activity.

The results showed that the deletion between the 0 to 99 (−900 to −801) nucleotides resulted in a decrease of about 30% in the promoter activity, while the deletion between the nucleotides 462 to 561 (−438 to −339) was about 20% in the promoter activity; deletion of the region 616 to 715 (−284 to −185) is about 70%; deletion of the region 693 to 792 (−207 to −108) is about 70%; deletion of the region 770 to 814 (−130 to −86) resulted in a decrease of about 30%. These regions, which cause a decrease in the promotor activity as a result of internal deletion analyzes, are the regions responsible for the positive regulation in the promoter activity (UAS, Upstream Activator Site).

Internal deletion between 539 to 638 (−361 to −262) nucleotides on SEQ ID NO: 1 caused a 63% increase in ADH3 promoter activity. This region in which deletion analysis results in increased promoter activity, is a region responsible for negative regulation in promoter activity (URS, Upstream Repressor Site).

Comparison of internal deletion analysis and 5' end-deletion analysis showed that internal deletion between 539 and 638 (−361 to −262) nucleotides resulted in a 63% increase in ADH3 promoter activity and 5' end-deletion analysis between −400 and −300 in the resulted in a 60% increase in the promoter activity, from about 70% to 130%.

No significant difference in activity was observed between 5' end-deletion analyzes between the 700 (−700 to 0), 600 (−600 to 0), 500 (−500 to 0), and 400 (−400 to 0) bp ADH3 promoters. The results indicated that there were no regulatory sequences in these regions responsible from promoter activity. Also, in internal deletion assays, when the DNA region between 200 and 500 (−700 to −400) in SEQ ID NO: 1 was deleted, the promoter activity was maintained at 94%. It has also been identified that mutations between the nucleotides 77 to 176 (−823 to −724), 154 to 253 (−746 to −647), 231 to 330 (−669 to −570), 308 to 407 (−592 to −493), 385 to 484 (−515 to −416) do not have a significant effect on promoter activity.

Figure 5:
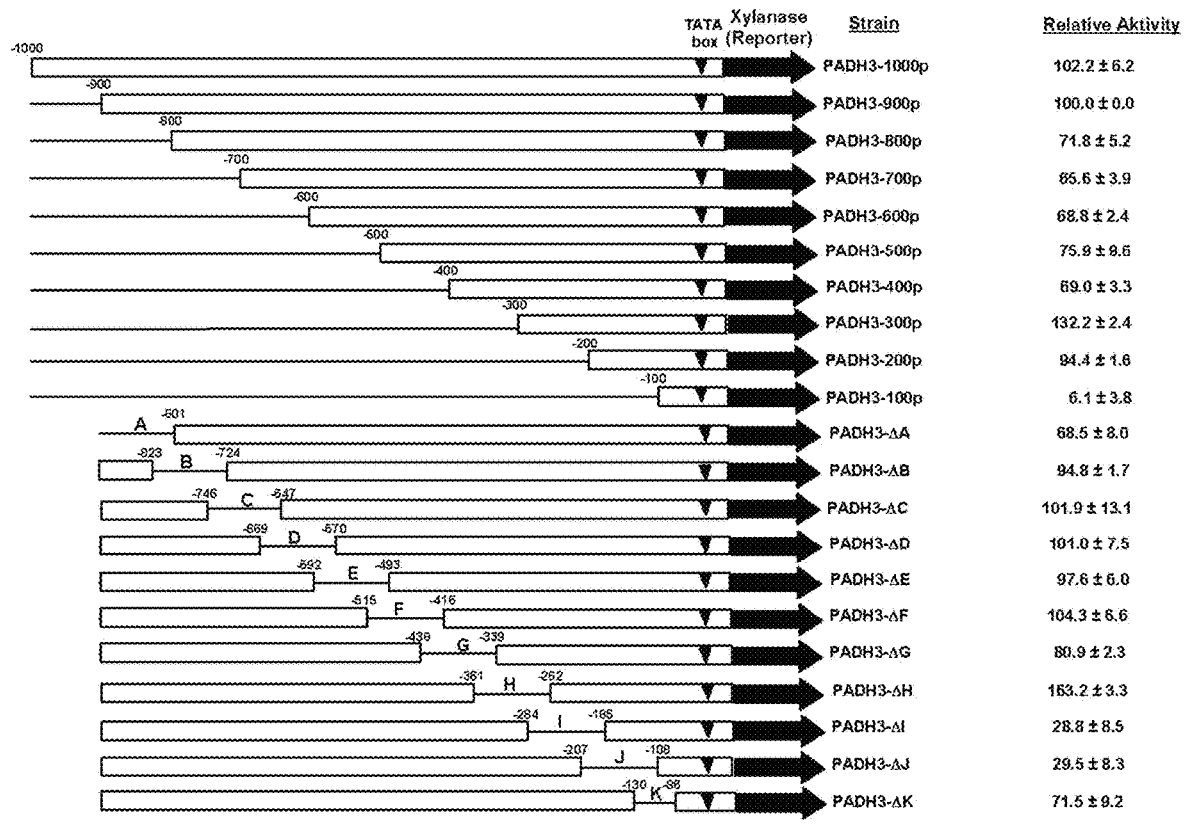
FIG. 5: Schematic representation of the deletion analyzes of the ADH3 promoter. It shows the deleted regions and promoter activities. XylB gene encoding xylanase was used as a reporter gene and promoter activities were determined by xylanase activity.

The present invention provides important data on the positive or negative regulatory regions on the ADH3 promoter. This data obtained by 5' end- and internal deletion analysis has been summarized in FIG. 5. Using this data, it is possible to obtain ADH3 promoters of different strengths.

Construction of Synthetic ADH3 Promoters

The results of the deletion assays identified nucleotides from 0 to 99 (−900 to −801) as UAS1; nucleotides 616 to 792 (−284 to −108) as UAS2; nucleotides 539 to 638 (−361 to −262) as URS1 on SEQ NO:1. Five different synthetic promoters were constructed using activator (UAS1 and UAS2) regions defined. All synthetic promoters created had a region of nucleotide 792 to 900 (−108 to 0) containing the ADH3 promoter TATA box. The ADH3-SNT5 promoter further comprises the fragment comprising the nucleotides from 100 to 538 (−800 to −362).

Enzyme recognition sites were used for combining the regions used in the construction of synthetic promoters. The regions included in the synthetic promoters and the endonuclease enzyme recognition sites used to combine these regions are shown schematically in FIG. 8.

Figure 8:
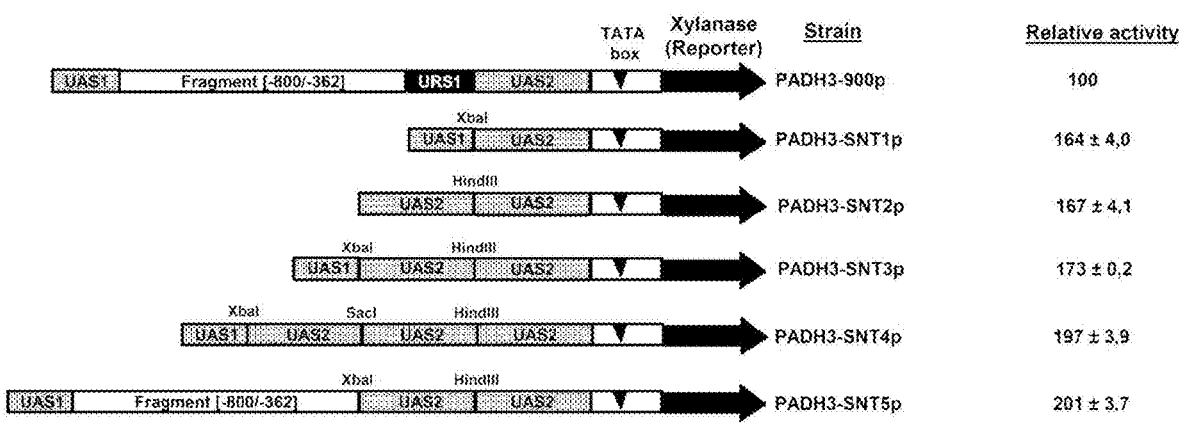
FIG. 8: Schematic representation of synthetic promoters. It shows the regions that make up the synthetic promoters, the endonuclease recognition regions used for the binding of the regions and the promoter activities obtained. XylB gene encoding xylanase was used as a reporter gene and promoter activities were determined by xylanase activity.

The regions used in the construction of the synthetic promoters were amplified by PCR method and the PCR products were digested with the enzymes of recognition regions shown in FIG. 8. The fragments were ligated from these regions using the ligase enzyme. The DNA sequences of the synthetic promoters constructed were given in Table 4.

TABLE 4

The DNA sequences of the synthetic promoters

| Promoter | SEQ ID No: |
| --- | --- |
| ADH3-SNT1 | 48 |
| ADH3-SNT2 | 49 |
| ADH3-SNT3 | 50 |
| ADH3-SNT4 | 51 |
| ADH3-SNT5 | 52 |

The resulting synthetic promoters were ligated to the expression vector by the strategy used in the deletion analysis (FIG. 1). The linearized plasmids are integrated into the *P. pastoris* GS115 his4 locus.

In the protein expression studies, the transformants were cultured in glycerol-containing medium at 28° C. for about 16 hours in shaking incubator. The grown cells were transferred to the ethanol medium in equal their optical densities and the supernatants were collected at the 8th hour of incubation. The activity of synthetic promoters was determined by measuring xylanase activity in supernatants. The results were calculated relatively by normalizing the promoter activities to that of 900 bp promoter defined as 100%.

The results showed that the promoter activities of ADH3-SNT1, ADH3-SNT2, ADH3-SNT3, ADH3-SNT4 and ADH3-SNT5 were 164%, 167%, 173%, 197% and 201%, respectively.

REFERENCES

Patents

U.S. Pat. No. 6,699,691 B2 March 2004 Inan et al.
U.S. Pat. No. 9,012,175 B2 April 2015 Hartner et al.
U.S. Pat. No. 8,222,386 B2 July 2012 Cregg et al.

Others

Chien, L. J., Lee, C. K. 2005. "Expression of bacterial hemoglobin in the yeast, *Pichia pastoris*, with a low O2-induced promoter", Biotechnology Letters, 27 (19), 1491-1497.

De Schutter, K., Lin Y. C., Tiels P., Van Hecke A., Glinka S., Weber-Lenhmann J., Rouze P., Peer Y., Van D. E. and Callewaert N. 2009. "Genome sequence of the recombinant protein production host *Pichia pastoris*", Nature Biotechnology, 27, 6, 561-566.

Karaoglan, M., Karaoglan, F. E., Inan, M. 2016a. "Comparison of ADH3 promoter with commonly used promoters for recombinant protein production in *Pichia pastoris*", Protein Expression and Purification, 121, 112-117.

Karaoglan, M., Karaoglan, F. E., Inan, M. 2016b. "Functional analysis of alcohol dehydrogenase (ADH) genes in *Pichia pastoris*", Biotechnology Letters, 38, 463-469.

Mattanovich, D., Graf, A., Stadlmann, J., Dragosits, M., Redl, A., Maurer, M., Kleinheinz, M., Sauer, M., Altmann, F., and Gasser B. 2009. "Genome, secretome and glucose transport highlight unique features of the protein production host *Pichia pastoris*", Microbial Cell Factories, June 2; 8:29.

Sambrook, J., and Russel D. 2001. Molecular Cloning: A Laboratory Manual. NY: Cold Spring Harbor Laboratory Press: Cold Spring Harbor.

Vogl, T. and Glieder A. 2013. "Regulation of *Pichia pastoris* promoters and its consequences for protein production", New Biotechnology, 30, 4, 385-404.

The invention claimed is:

1. A mutant ADH3 promoter, characterized by comprising the nucleotide sequence of SEQ ID NO: 52.

2. A vector comprising a mutant ADH3 promoter according to claim 1 and a functional nucleic acid sequence, wherein the vector is pADH3ZαA and/or pADH3ZαA-XylB/HIS4.

3. A host cell, characterized by comprising a vector according to claim 2.

* * * * *